(12) United States Patent
Iwabuchi et al.

(10) Patent No.: US 9,199,970 B2
(45) Date of Patent: Dec. 1, 2015

(54) 4-[5-(PYRIDIN-4-YL)-1H-1,2,4-TRIAZOL-3-YL]PYRIDINE-2-CARBONITRILE CRYSTALLINE POLYMORPH AND PRODUCTION METHOD THEREFOR

(71) Applicant: FUJIYAKUHIN CO., LTD., Saitama-shi (JP)

(72) Inventors: Yoshiyuki Iwabuchi, Saitama (JP); Sachiho Miyata, Saitama (JP); Takahiro Sato, Saitama (JP); Junichiro Uda, Saitama (JP); Takamitsu Kandou, Saitama (JP); Tadashi Inoue, Saitama (JP); Hiroyuki Nakano, Saitama (JP)

(73) Assignee: FUJIYAKUHIN CO., LTD., Saitama-shi (JP)

( * ) Notice: Subject to any disclaimer, the term of this patent is extended or adjusted under 35 U.S.C. 154(b) by 0 days.

(21) Appl. No.: 14/407,739

(22) PCT Filed: Jul. 24, 2013

(86) PCT No.: PCT/JP2013/070004
§ 371 (c)(1),
(2) Date: Dec. 12, 2014

(87) PCT Pub. No.: WO2014/017515
PCT Pub. Date: Jan. 30, 2014

(65) Prior Publication Data
US 2015/0126558 A1    May 7, 2015

(30) Foreign Application Priority Data

Jul. 25, 2012  (JP) ................................. 2012-177539

(51) Int. Cl.
*C07D 401/14*  (2006.01)

(52) U.S. Cl.
CPC ................................. *C07D 401/14* (2013.01)

(58) Field of Classification Search
CPC ...................................................... C07D 401/14
USPC ......................................... 546/256; 514/333
See application file for complete search history.

(56) References Cited

U.S. PATENT DOCUMENTS

| 6,627,646 | B2 * | 9/2003 | Bakale et al. ................. 514/322 |
| 2002/0048610 | A1 | 4/2002 | Cima et al. |
| 2002/0098518 | A1 | 7/2002 | Levinson |
| 2002/0177167 | A1 | 11/2002 | Levinson et al. |
| 2003/0059837 | A1 | 3/2003 | Levinson et al. |
| 2003/0106492 | A1 | 6/2003 | Levinson et al. |
| 2003/0123057 | A1 | 7/2003 | Lemmo et al. |
| 2003/0138940 | A1 | 7/2003 | Lemmo et al. |
| 2003/0162226 | A1 | 8/2003 | Cima et al. |
| 2004/0252299 | A9 | 12/2004 | Lemmo et al. |
| 2005/0004175 | A1 | 1/2005 | Nakamura et al. |
| 2005/0130220 | A1 | 6/2005 | Lemmo et al. |
| 2005/0191614 | A1 | 9/2005 | Cima et al. |
| 2006/0141533 | A1 | 6/2006 | Levinson |
| 2006/0189811 | A1 | 8/2006 | Nakamura et al. |
| 2007/0020662 | A1 | 1/2007 | Cima et al. |
| 2007/0021929 | A1 | 1/2007 | Lemmo et al. |

FOREIGN PATENT DOCUMENTS

| JP | 2003 519698 | 6/2003 |
| JP | 2005 41802 | 2/2005 |
| WO | 03 064410 | 8/2003 |
| WO | 2005 009991 | 2/2005 |

OTHER PUBLICATIONS

CMU Pharmaceutical polymorphism, internet p. 1-3 (2002) printout Apr. 3, 2008.*
Singhal et al., "Drug Polymorphism, etc.," Advanced Drug Delivery reviews 56, p. 335-347 (2004).*
Concise Encyclopedia Chemistry, NY: Walter de Gruyter, 1993, 872-873.*
Jain et al., "Polymorphism in Pharmacy", Indian Drugs, 1986, 23(6) 315-329.*
Muzaffar et al., "Polymorphism and Drug Availability, etc.," J of Pharm. (Lahore), 1979, 1(1), 59-66.*
U.S. Pharmacopia #23, National Formulary #18, 1995, 1843-1844.*
Doelker, english translation of S.T.P, Pratiques (1999), 9(5), 399-409, pp. 1-33.*
Doelker, english translation of Ann. Pharm. Fr., 2002, 60: 161-176, pp. 1-39.*
Taday et al., "Using Terahertz, etc.," J of Pharm. Sci., 92(4), 2003, 831-838.*
Otuska et al., "Effect of Polymorphic, etc.," Chem. Pharm. Bull., 47(6) 852-856 (1999).*
Written Opinion of the International Searching Authority Issued Nov. 5, 2013 in PCT/JP13/070004 Filed Jul. 24, 2013.
International Search Report Issued Nov. 5, 2013 in PCT/JP13/070004 Filed Jul. 24, 2013.

* cited by examiner

*Primary Examiner* — Patricia L Morris
(74) *Attorney, Agent, or Firm* — Oblon, McClelland, Maier & Neustadt, L.L.P.

(57) ABSTRACT

To provide crystal polymorphs of 4-[5-(pyridin-4-yl)-1H-1,2,4-triazol-3-yl]pyridine-2-carbonitrile, which is a useful pharmaceutical, and a production method therefor. Through purification of a corresponding salt, recrystallization, or storage under humidified conditions, three different crystal forms; i.e., crystalline polymorphs of 4-[5-(pyridin-4-yl)-1H-1,2,4-triazol-3-yl]pyridine-2-carbonitrile are produced.

2 Claims, 8 Drawing Sheets

4-[5-(PYRIDIN-4-YL)-1H-1,2,4-TRIAZOL-3-YL]PYRIDINE-2-CARBONITRILE CRYSTALLINE POLYMORPH AND PRODUCTION METHOD THEREFOR

TECHNICAL FIELD

The present invention relates to a crystalline polymorph of 4-[5-(pyridin-4-yl)-1H-1,2,4-triazol-3-yl]pyridine-2-carbonitrile and to a production method therefor.

BACKGROUND ART

Compound (1), 4-[5-(pyridin-4-yl)-1H-1,2,4-triazol-3-yl]pyridine-2-carbonitrile, is known to serve as a drug which has a xanthine oxidase inhibitory action and which can lower serum uric acid level (Patent Document 1).

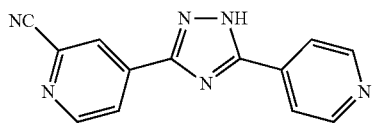

(1)

There have been reported several methods for producing the above compound (1). In one production method, methyl isonicotinate N-oxide is subjected to Reissert Henze reaction, to thereby form methyl 2-cyanoisonicotinate, which is transformed into a hydrazide, and the hydrazide is condensed with 4-cyanopyridine (Patent Document 1, Example 12). In another production method, isonicotinic acid N-oxide is transformed into a hydrazide, into which a cyano group is incorporated through Reissert Henze reaction, and the product is condensed with 4-cyanopyridine (Patent Document 1, Example 39). In an alternative production method, 4-cyanopyridine-N-oxide (starting material) is condensed with isonicotinic acid hydrazide, to thereby form a triazole ring, which is then protected (Patent Document 2) or non-protected (Patent Document 3), and a cyano group is incorporated into the product through Reissert Henze reaction, to thereby yield compound (1).

Meanwhile, crystalline polymorphism means such a condition that a compound formed of a unique molecule having a unique chemical composition exists in two or more crystal forms having different molecular arrangements. When a pharmaceutical compound is such a compound, pharmacological activity, solubility, bioavailability, stability, and the like of the compound are known to vary depending on the physicochemical properties intrinsic to the polymorph. Thus, when the useful pharmaceutical compound includes crystalline polymorphs, a compound of a crystal form which provides high utility is preferably produced.

CITATION LIST

Patent Document

Patent Document 1: WO2003/064410
Patent Document 2: WO2005/009991
Patent Document 3: JP-A-2005-41802

SUMMARY OF THE INVENTION

Problems to be Solved by the Invention

However, the aforementioned Patent Documents disclose production methods for 4-[5-(pyridin-4-yl)-1H-1,2,4-triazol-3-yl]pyridine-2-carbonitrile, but do not disclose crystalline polymorphism of the compound. The disclosed production methods are provided for the purpose of enhancement in yield and chemical purity. That is, these patent documents describe no crystallographic aspect of the compound.

Thus, an object of the present invention is to provide a pharmaceutically useful novel crystal form of 4-[5-(pyridin-4-yl)-1H-1,2,4-triazol-3-yl]pyridine-2-carbonitrile, whose crystalline polymorphism has not yet been elucidated. Another object is to provide a production method therefor.

Means for Solving the Problems

The present inventors have conducted extensive studies in order to solve the aforementioned problems, and have found that treating free 4-[5-(pyridin-4-yl)-1H-1,2,4-triazol-3-yl]pyridine-2-carbonitrile with an acid, to form a corresponding salt, treating the salt with a base, and neutralizing the base-treated product with an acid can yield type I crystals thereof. The inventors have also found that recrystallizing free 4-[5-(pyridin-4-yl)-1H-1,2,4-triazol-3-yl]pyridine-2-carbonitrile from an organic solvent can yield type II crystals thereof. The inventors have also found that storing free 4-[5-(pyridin-4-yl)-1H-1,2,4-triazol-3-yl]pyridine-2-carbonitrile under humidified conditions can yield a hydrate thereof.

Accordingly, the present invention provides the following [1] to [9].
[1] Type I crystals of 4-[5-(pyridin-4-yl)-1H-1,2,4-triazol-3-yl]pyridine-2-carbonitrile exhibiting characteristic peaks in powder X-ray diffractometry at diffraction angles (2θ) of about 10.1°, 16.0°, 20.4°, 25.7°, and 26.7°.
[2] Type II crystals of 4-[5-(pyridin-4-yl)-1H-1,2,4-triazol-3-yl]pyridine-2-carbonitrile exhibiting characteristic peaks in powder X-ray diffractometry at diffraction angles (2θ) of about 9.9°, 16.3°, 18.2°, and 22.4°.
[3] A hydrate of 4-[5-(pyridin-4-yl)-1H-1,2,4-triazol-3-yl]pyridine-2-carbonitrile exhibiting characteristic peaks in powder X-ray diffractometry at diffraction angles (2θ) of about 8.1°, 14.9°, 16.4°, 25.3°, 26.9°, and 27.6°.
[4] A method for producing type I crystals of 4-[5-(pyridin-4-yl)-1H-1,2,4-triazol-3-yl]pyridine-2-carbonitrile, the method comprising treating an acid salt of 4-[5-(pyridin-4-yl)-1H-1,2,4-triazol-3-yl]pyridine-2-carbonitrile with a base and subsequently neutralizing the treated product with an acid.
[5] A method for producing type II crystals of 4-[5-(pyridin-4-yl)-1H-1,2,4-triazol-3-yl]pyridine-2-carbonitrile, the method comprising recrystallizing 4-[5-(pyridin-4-yl)-1H-1,2,4-triazol-3-yl]pyridine-2-carbonitrile from an organic solvent.
[6] A method for producing a hydrate of 4-[5-(pyridin-4-yl)-1H-1,2,4-triazol-3-yl]pyridine-2-carbonitrile, the method comprising storing 4-[5-(pyridin-4-yl)-1H-1,2,4-triazol-3-yl]pyridine-2-carbonitrile under humidified conditions.
[7] A pharmaceutical composition comprising the type I crystals as recited in [1] above, and a pharmaceutically acceptable carrier.
[8] A pharmaceutical composition comprising the type II crystals as recited in [2] above, and a pharmaceutically acceptable carrier.
[9] A pharmaceutical composition comprising the hydrate as recited in [3] above, and a pharmaceutically acceptable carrier.

Effects of the Invention

The present invention enables provision of type I crystals, type II crystals, and a hydrate of 4-[5-(pyridin-4-yl)-1H-1,2,4-triazol-3-yl]pyridine-2-carbonitrile, which are useful pharmaceuticals.

The present invention enables provision of methods for separately producing type I crystals, type II crystals, and a hydrate of 4-[5-(pyridin-4-yl)-1H-1,2,4-triazol-3-yl]pyridine-2-carbonitrile.

In particular, the type I crystals thereof are more useful than the other crystal forms, from the viewpoints of industrial superiority, solubility, and crystal form stability.

MODES FOR CARRYING OUT THE INVENTION

Figure 1:
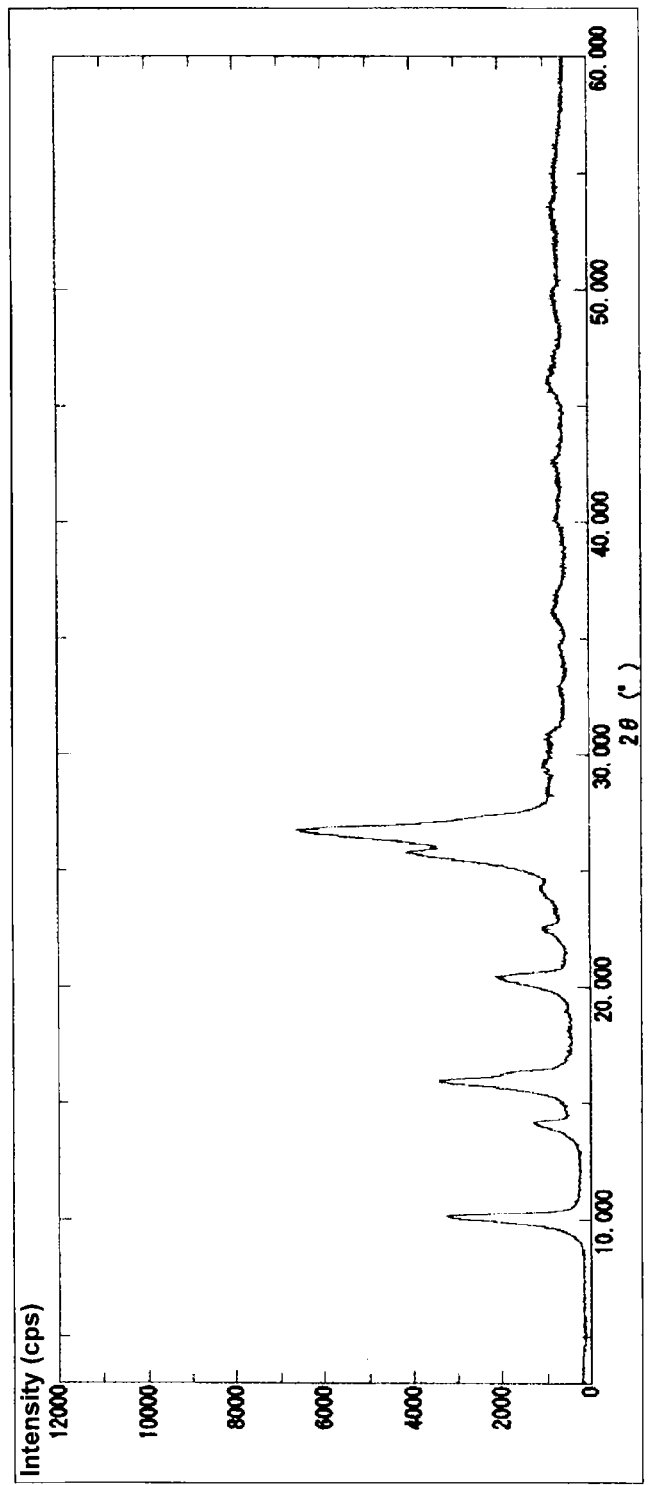
FIG. 1 An powder X-ray diffraction pattern of type I crystals.

The present invention will next be described in detail.

Type I crystals of 4-[5-(pyridin-4-yl)-1H-1,2,4-triazol-3-yl]pyridine-2-carbonitrile (hereinafter referred to as compound (1)) are produced through treating an acid salt of compound (1) with a base and neutralizing the treated product with an acid.

Examples of the acid salt of compound (1) include inorganic acid salts such as hydrochloride, sulfate, and phosphate; and organic acid salts such as oxalate, malonate, succinate, acetate, and p-toluenesulfonate. Of these, the p-toluenesulfonate is preferred. These acid salts may be produced through any method disclosed in Patent Documents 1 to 3.

In a preferred mode of the base treatment of the acid salt of compound (1), a base is dissolved in a solvent, and the acid salt of compound (1) is added to the solution. Examples of the solvent which can solve the acid salt of compound (1) include protic solvents such as water, methanol, ethanol, isopropanol, 1-butyl alcohol, 2-methyl-1-propanol, 2-butanol, 2-methyl-2-propanol, and ethylene glycol. In use, these solvents may be mixed at any ratio, to thereby provide a mixed solvent. Among these solvents, a water-alcohol mixed solvent is preferred, with a water-ethanol (3:1 to 10:1) mixed solvent being more preferred.

No particular limitation is imposed on the amount, temperature, etc. of the aforementioned solvent, so long as the amount, temperature, etc. allow the acid salt of compound (1) to be dissolved therein.

Any base may be used in the base treatment of the acid salt of compound (1), so long as the base can render the solution of the acid salt of compound (1) to be weakly basic. Examples of the base include inorganic bases such as sodium hydroxide, potassium hydroxide, sodium carbonate, potassium carbonate, trisodium phosphate, and tripotassium phosphate; and tertiary amines such as triethylamine and diisopropylethylamine. Of these, potassium carbonate and tripotassium phosphate are preferred.

These bases are preferably used in an amount of 2 to 5 mol, more preferably in an amount of 2 to 4 mol, with respect to 1 mol of the acid salt of compound (1).

For neutralizing the base-treated solution, an acid such as citric acid, hydrochloric acid, sulfuric acid, or phosphoric acid may be used. Of these, hydrochloric acid is preferred.

No particular limitation is imposed on the reaction temperature in neutralization with acid. However, the temperature is preferably −10° C. to 30° C., more preferably 20 to 30° C.

Through neutralization with acid, type I crystals of compound (1) are precipitated. Type I crystals of compound (1) may be recovered though drying under reduced pressure with heating.

Type II crystals of compound (1) may be produced through recrystallization of compound (1) from an organic solvent. Examples of the recrystallization solvent include methanol, ethanol, 1-propanol, isopropanol, 1-butyl alcohol, 2-methyl-1-propanol, 2-butanol, 2-methyl-2-propanol, tetrahydrofuran, acetone, N,N-dimethylformamide, N,N-dimethylacetamide, dimethylsulfoxide, ethyl acetate, ether, diisopropyl ether, chloroform, hexane, cyclohexane, heptane, octane, benzene, toluene, and xylene. These solvents may be used singly or in combination of two or more species. The aforementioned recrystallization solvent is preferably an amide-type solvent, more preferably N,N-dimethylformamide. Recrystallization may be carried out by dissolving compound (1) at 60 to 160° C., preferably at 120 to 150° C., and then cooling the solution to 15 to 40° C., preferably to 20 to 30° C.

A hydrate of compound (1) may be produced by storing compound (1) under high humidity conditions (e.g., 20 to 30° C., relative humidity (RH): 85% to 97%). The storage time is at least 10 days.

The afore-yielded type I crystals of compound (1) exhibits characteristic peaks in a powder X-ray diffraction pattern at diffraction angles (2θ) of about 10.1°, 16.0°, 20.4°, 25.7°, and 26.7°. The powder X-ray diffraction spectral pattern is shown in FIG. 1.

Figure 4:
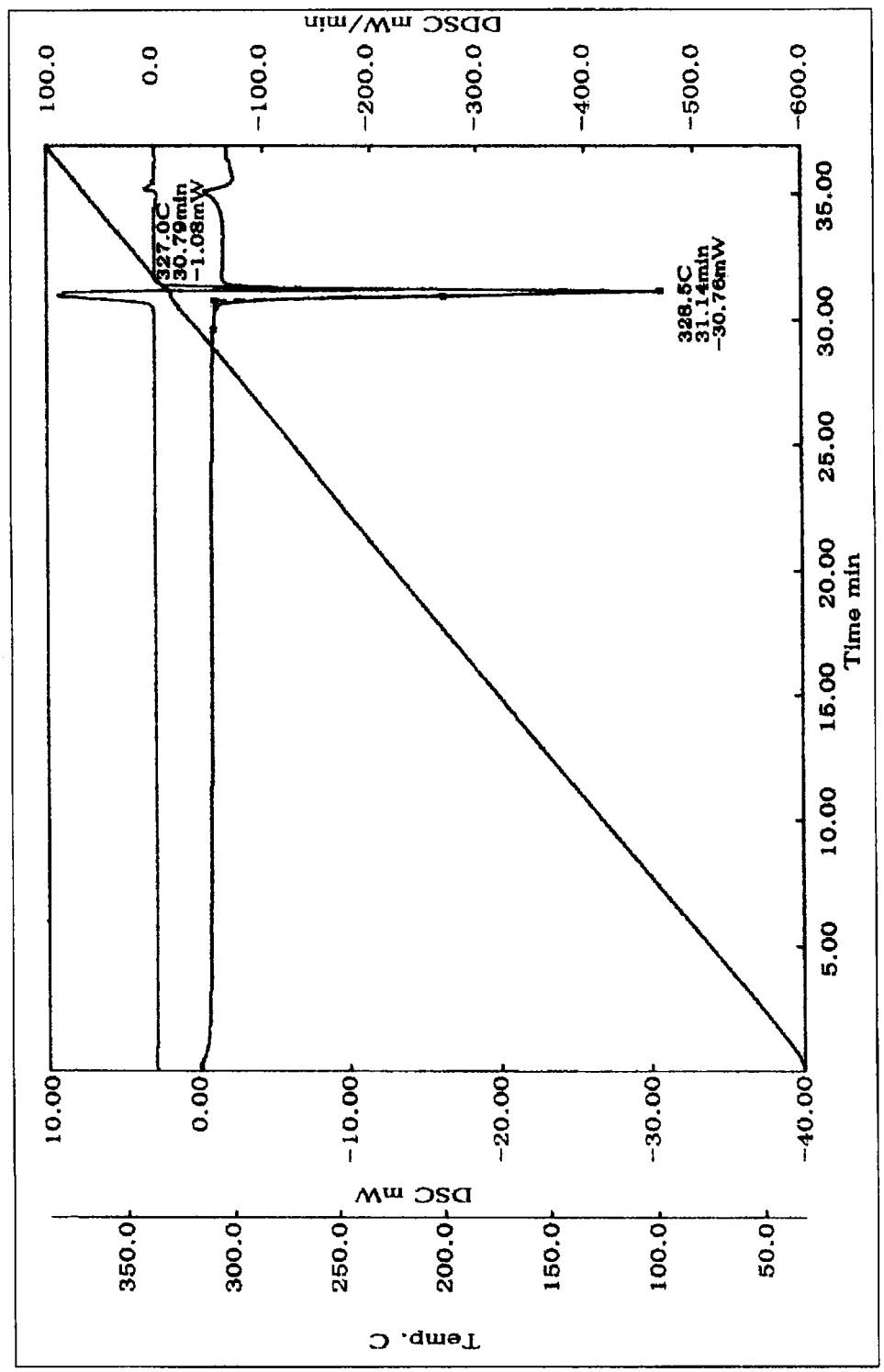
FIG. 4 Differential scanning calorimetry (DSC) pattern of type I crystals.

The DSC pattern of FIG. 4 has an endothermic peak at about 327° C.

Figure 2:
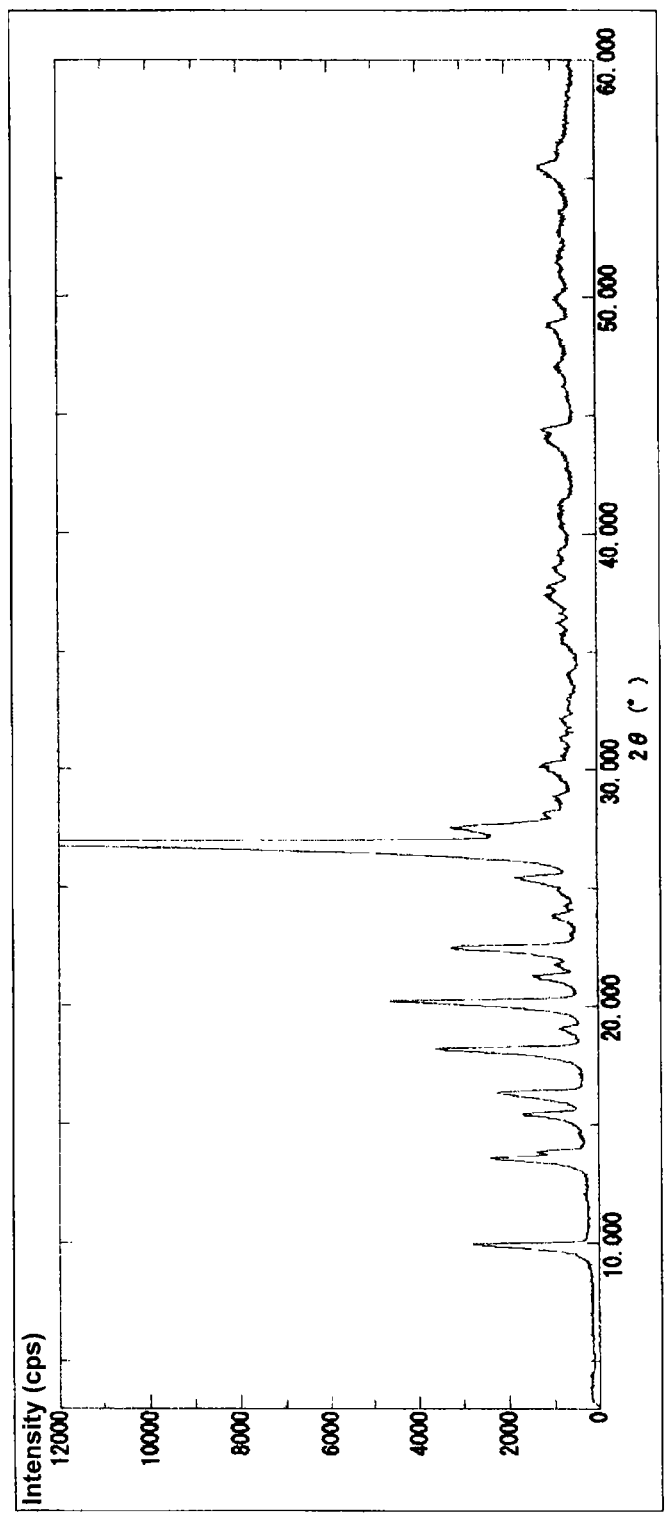
FIG. 2 An powder X-ray diffraction pattern of type II crystals.

The afore-yielded type II crystals of compound (1) exhibits characteristic peaks in a powder X-ray diffraction pattern at diffraction angles (2θ) of about 9.9°, 16.3°, 18.2°, and 22.4°. The powder X-ray diffraction spectral pattern is shown in FIG. 2.

Figure 5:
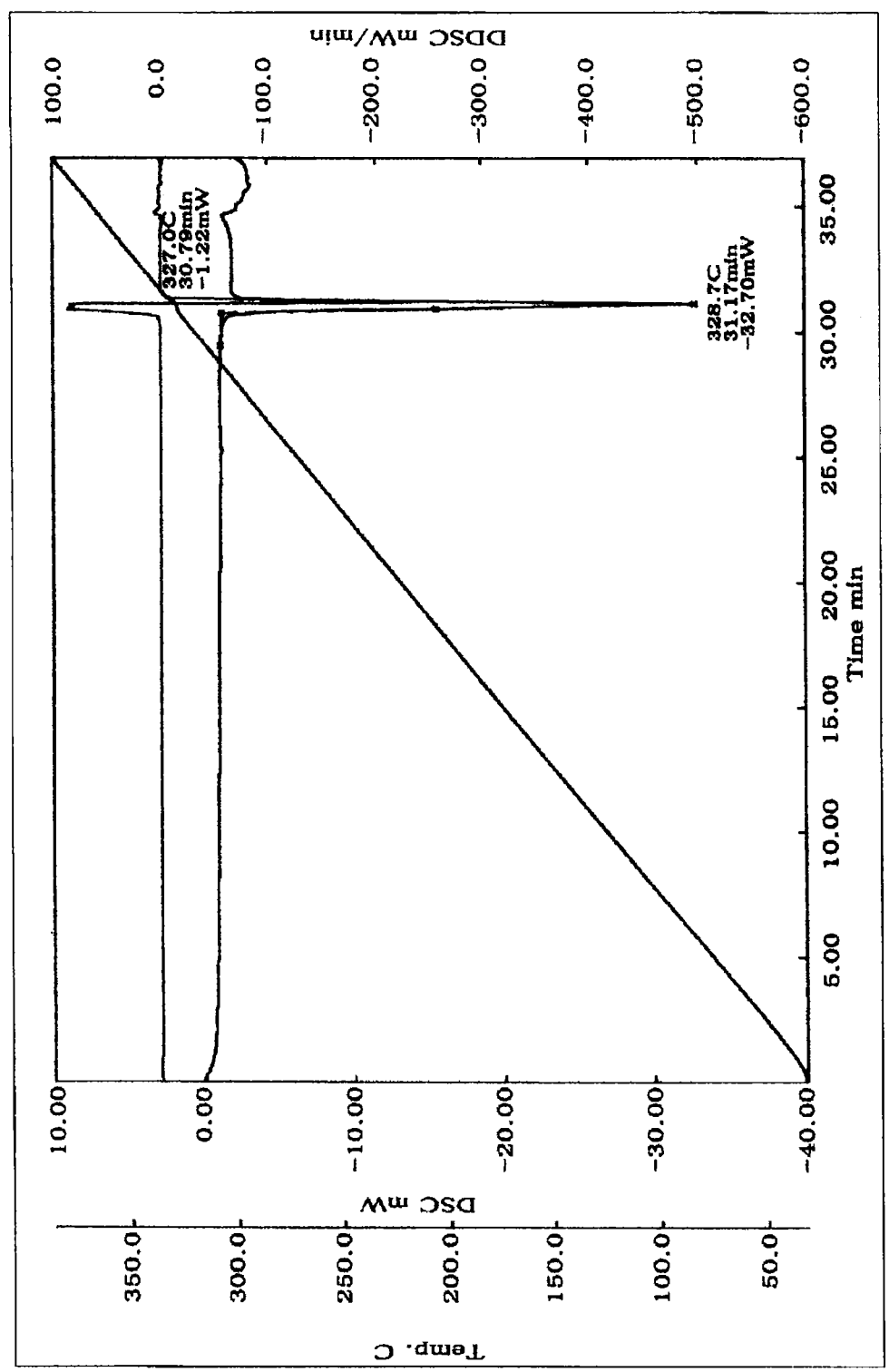
FIG. 5 Differential scanning calorimetry (DSC) pattern of type II crystals.
Figure 6:
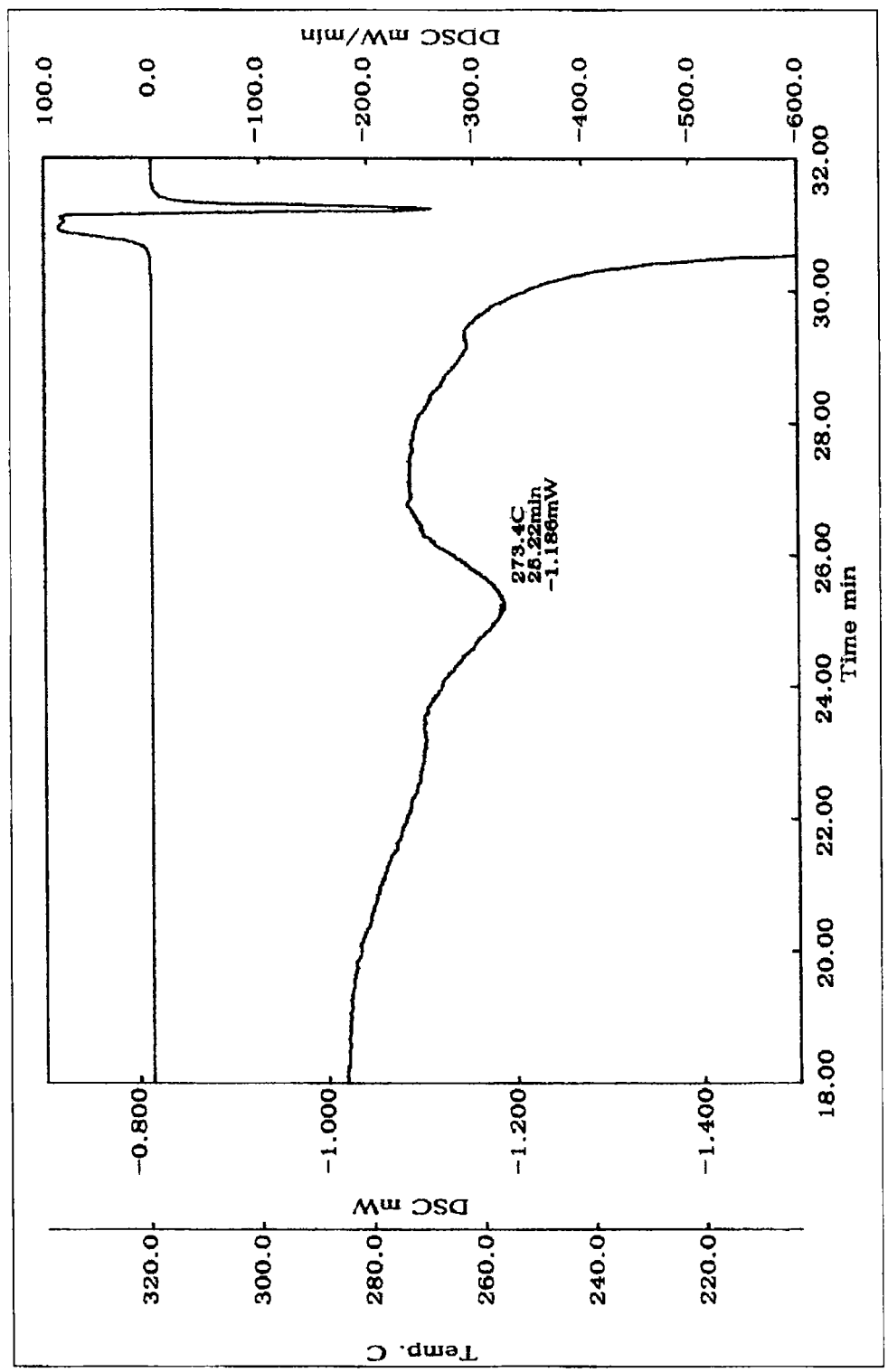
FIG. 6 Differential scanning calorimetry (DSC) (enlarged) pattern of type II crystals.

The DSC pattern of FIG. 5 has an endothermic peak at about 327° C., and that of FIG. 6 has an endothermic peak at about 273° C.

Figure 3:
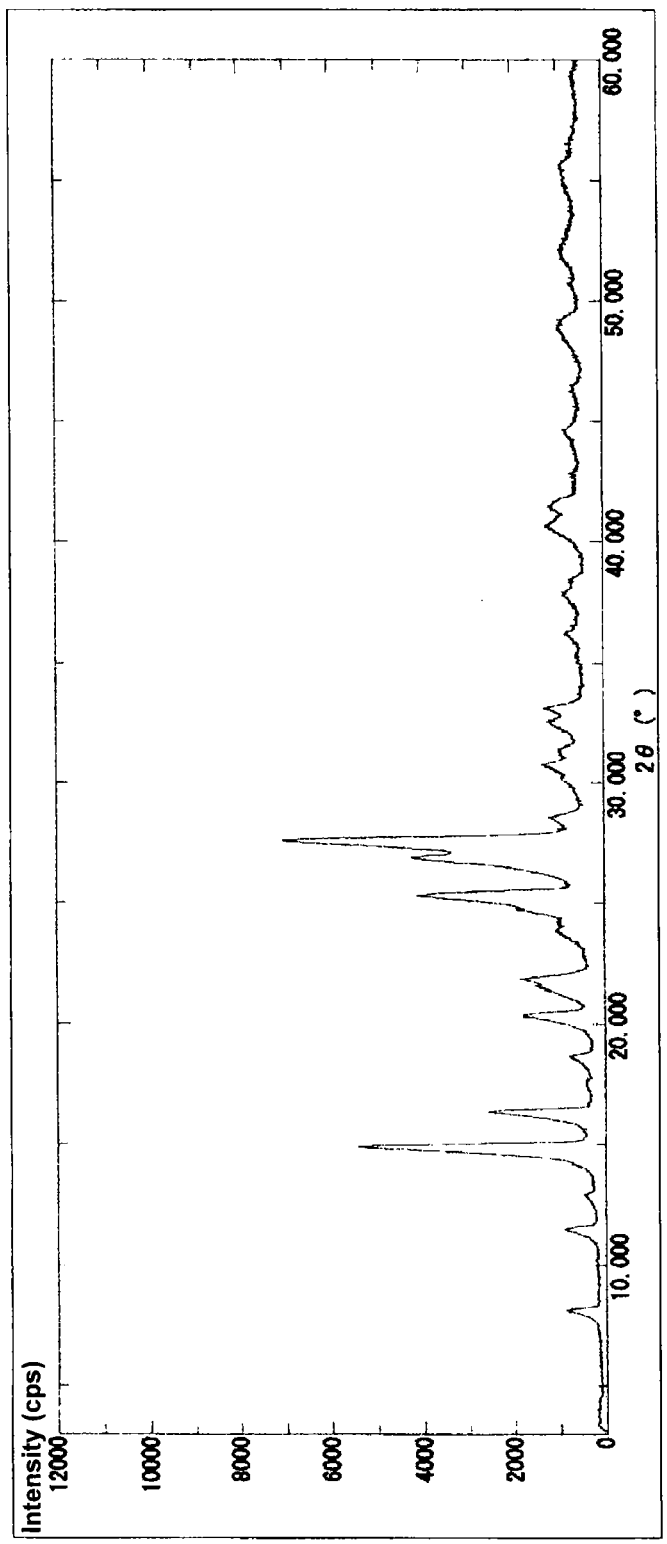
FIG. 3 An powder X-ray diffraction pattern of the hydrate.

The hydrate of compound (1) exhibits characteristic peaks in a powder X-ray diffraction pattern at diffraction angles (2θ) of about 8.1°, 14.9°, 16.4°, 25.3°, 26.9°, and 27.6°. The powder X-ray diffraction spectral pattern is shown in FIG. 3.

Figure 7:
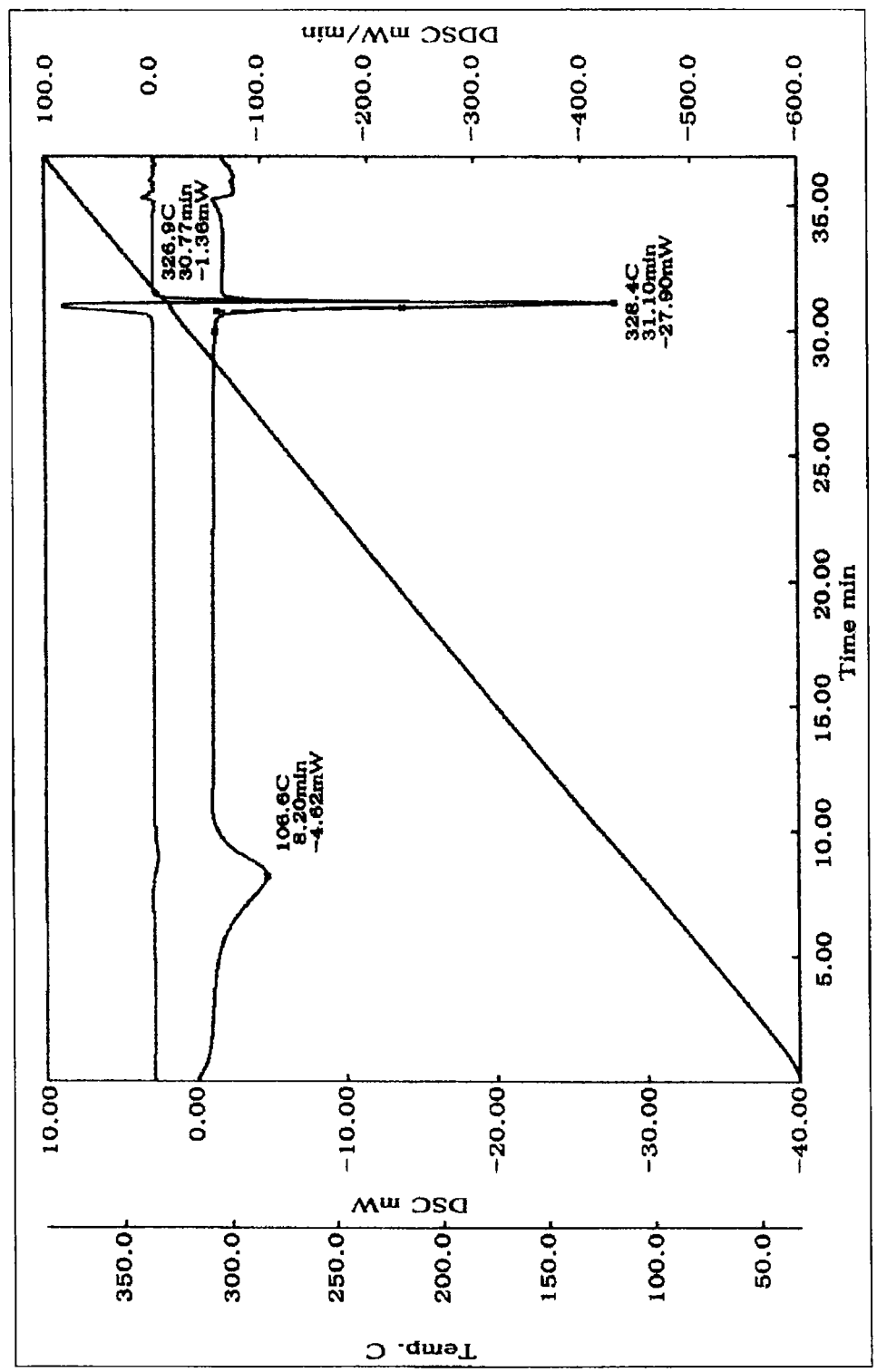
FIG. 7 Differential scanning calorimetry (DSC) pattern of the hydrate.

The DSC pattern of FIG. 7 has endothermic peaks at about 107° C. and 327° C.

The hydrate of compound (1) is preferably a monohydrate thereof.

In the present invention, the powder X-ray diffraction spectrum refers to a spectrum measured by means of Mini Flex (product of Rigaku Corporation) under the following conditions.

X-ray source: Cu
Goniometer: vertical
Divergence slit: variable
Scattering slit: 4.2 degree
Receiving slit: 0.3 mm
Scanning mode: continuous
Scanning speed: 2°/min
Scanning step: 0.02°
Scanning axis: θ/2θ
Scanning range: 3 to 60°

Endothermic peaks of DSC refer to those measured by means of DSC 220U (product of Seiko Instruments Inc.) under the following conditions.

Temperature elevation rate: 10° C./min
Atmosphere: nitrogen
Measurement temperature range: 30 to 400° C.

When the crystals of compound (1) are analyzed by means of the aforementioned apparatuses, crystal forms of compound (1) which have data and spectral patterns similar to one another are categorized into the same crystal form of the present invention. Also, when the type I crystals of compound (1), the type II crystals of compound (1), or the hydrate of compound (1) of the present invention contains another crystal form in such a small amount as not to be detected through a routine measurement method, it is also categorized into the same crystal form of the present invention.

Furthermore, physical property data of powder X-ray diffraction spectra, DSC, etc. might vary slightly due to variation in measurement factors such as crystal growth direction and particle size. Principally, the crystal form of compound (1) of the present invention should be determined by physical property data disclosed in the specification. However, as described above, this principle should not be strict, and slight variation in data of physical properties may be allowed. For example, an angle variation of ±0.5° in X-ray diffraction falling within an allowable range should be included in the scope of rights of the present invention.

Among crystal forms of compound (1) of the present invention, type I crystals are particularly preferred, from the viewpoints of high water solubility and excellent thermal stability.

The crystal forms of compound (1) of the present invention have excellent water-solubility and thermal stability. Thus, any of the crystal forms can be processed into various pharmaceutical compositions by mixing with a pharmaceutically acceptable carrier. Such a pharmaceutical composition is preferably a solid preparation, particularly preferably a per-oral solid preparation.

In production of a peroral solid preparation, crystals of compound (1) are mixed with an optional additive such as a vehicle, a binder, a disintegrator, a lubricant, a colorant, a coating agent, a wetting agent, a sugar coating agent, an antiseptic agent, a preservative, an antioxidant, or a flavoring agent/corrigent. The thus-obtained mixture is formed into preparations in the form of tablet, coated-tablet, granule, powder, capsule, or the like.

The pharmaceutical composition of the present invention is useful as a uric acid level reducing agent or a gout prophylactic/therapeutic agent.

EXAMPLES

The present invention will next be described in detail by way of Examples and Test Example, which should not be construed as limiting the invention thereto.

In the Examples, used are the following abbreviations: $^1$H-NMR: proton nuclear magnetic resonance spectrum, DMSO-$d_6$: deuterated dimethylsulfoxide, Hz: hertz, J: coupling constant, s: singlet, dd: double doublet, and m: multiplet. The "NMR" refers to a 270 MHz nuclear magnetic resonance spectrum measured by use of TMS (tetramethylsilane) as an internal standard.

Example 1

Synthesis of 4-[5-(pyridin-4-yl)-1H-1,2,4-triazol-3-yl]pyridine-2-carbonitrile p-toluenesulfonate p-Toluenesulfonic acid monohydrate (6.62 g) was added to a water-2-butanol (10:1) mixture (55 mL). Subsequently, 4-[5-(pyridin-4-yl)-1H-1,2,4-triazol-3-yl]pyridine-2-carbonitrile (7.85 g) was added thereto at 80° C., and the resultant mixture was stirred at 80° C. for 1 hour. The reaction mixture was cooled to room temperature, and the precipitated crystals were recovered through filtration. The crystals were washed with a water-2-butanol (10:1) mixture (40 mL) and dried at 80° C. for 10 hours under reduced pressure, to thereby yield 12.6 g of 4-[5-(pyridin-4-yl)-1H-1,2,4-triazol-3-yl]pyridine-2-carbonitrile p-toluenesulfonate.

$^1$H-NMR (DMSO-$d_6$) δ(ppm): 2.29 (s, 3H), 7.11 (m, 2H), 7.48 (dd, 2H, J=6.48, 1.62 Hz), 8.32-8.35 (m, 3H), 8.57 (dd, 1H, J=1.62, 0.81 Hz), 8.94-8.98 (m, 3H)

Example 2

Preparation of Type I Crystals

Potassium carbonate (8.22 g) and 4-[5-(pyridin-4-yl)-1H-1,2,4-triazol-3-yl]pyridine-2-carbonitrile p-toluenesulfonate (10.0 g) were dissolved in a water-ethanol (9:1) mixture (80 mL). 6M hydrochloric acid (15 mL) was added to the solution, and the resultant mixture was stirred at 20° C. for 5 hours. The precipitated crystals were recovered through filtration and washed with water (100 mL). The crystals were dried at 80° C. for 23 hours under reduced pressure, to thereby yield 5.78 g of 4-[5-(pyridin-4-yl)-1H-1,2,4-triazol-3-yl]pyridine-2-carbonitrile. The thus-obtained crystals exhibited a powder X-ray diffraction pattern shown in FIG. 1 and a DSC profile shown in FIG. 4, indicating that the crystals were type I crystals.

$^1$H-NMR (DMSO-$d_6$) δ(ppm): 8.02 (dd, 2H, J=4.59, 1.62 Hz), 8.32 (dd, 1H, J=5.13, 1.62 Hz), 8.55 (dd, 1H, J=1.62, 1.08 Hz), 8.80 (dd, 2H, =4.59, 1.62 Hz), 8.93 (dd, 1H, 5.13, 1.08 Hz)

Melting point: 327° C.

Example 3

Preparation of Type II Crystals

N,N-dimethylformamide (300 mL) was added to 4-[5-(pyridin-4-yl)-1H-1,2,4-triazol-3-yl]pyridine-2-carbonitrile (40.0 g), and the mixture was stirred at 150° C. for 25 minutes. The thus-obtained solution was cooled to room temperature, and the precipitated crystals were recovered through filtration. The crystals were washed twice with water (200 mL) and dried overnight at 80° C. under reduced pressure, to thereby yield 30.4 g of 4-[5-(pyridin-4-yl)-1H-1,2,4-triazol-3-yl]pyridine-2-carbonitrile. The thus-obtained crystals exhibited a powder X-ray diffraction pattern shown in FIG. 2 and a DSC profile shown in FIG. 5, indicating that the crystals were type II crystals.

$^1$H-NMR (DMSO-$d_6$) δ(ppm): 8.02 (dd, 2H, J=4.59, 1.62 Hz), 8.32 (dd, 1H, J=5.13, 1.62 Hz), 8.55 (dd, 1H, J=1.62, 1.08 Hz), 8.80 (dd, 2H, J=4.59, 1.62 Hz), 8.93 (dd, 1H, 5.13, 1.08 Hz)

Melting point: 327° C.

Example 4

Preparation of Hydrate

4-[5-(Pyridin-4-yl)-1H-1,2,4-triazol-3-yl]pyridine-2-carbonitrile (about 2 g) was stored at 25° C. and an RH of 97% for 14 days. The thus-obtained crystals exhibited a powder X-ray diffraction pattern shown in FIG. 3 and a DSC profile shown in FIG. 7, indicating that the crystals were in a hydrate form.

$^1$H-NMR (DMSO-$d_6$) δ(ppm): 8.02 (dd, 2H, J=4.59, 1.62 Hz), 8.32 (dd, 1H, J=5.13, 1.62 Hz), 8.55 (dd, 1H, J=1.62, 1.08 Hz), 8.80 (dd, 2H, J=4.59, 1.62 Hz), 8.93 (dd, 1H, 5.13, 1.08 Hz)

Melting point: 327° C.

Test Example

Solubility Test of Various Crystal Forms

Figure 8:
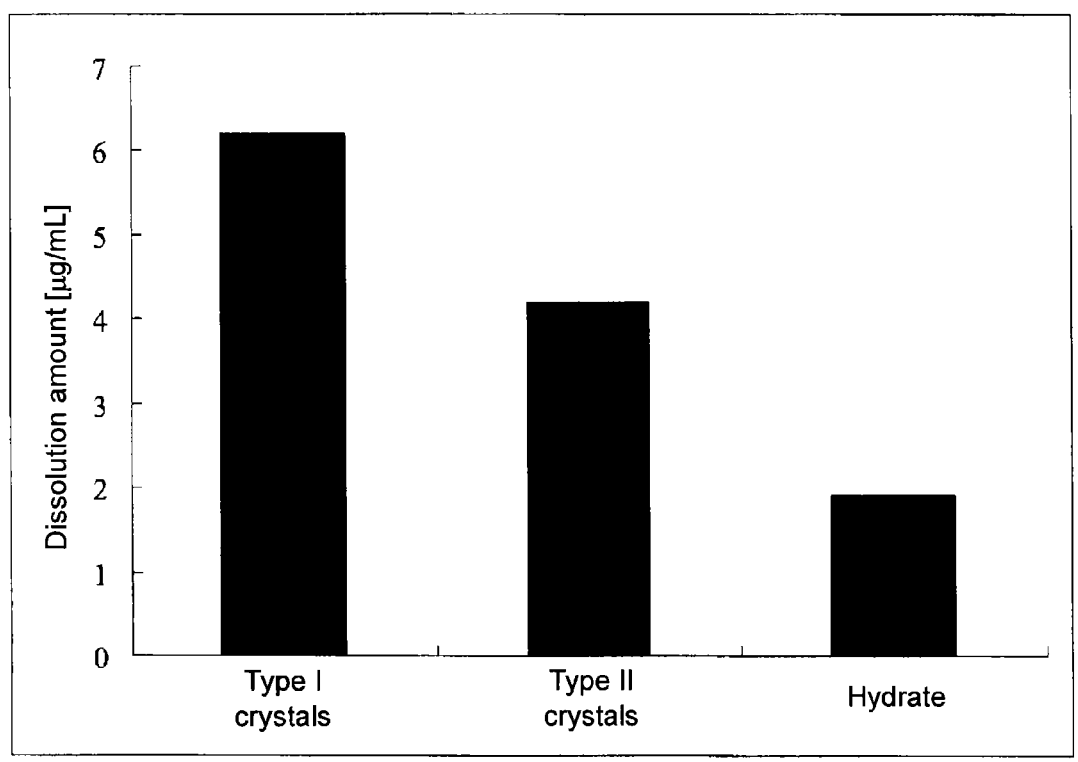
FIG. 8 Solubility test results of various crystal forms.

The water solubilities of type I crystals, type II crystals, and the hydrate of compound (1) were determined by calculating each sample concentration of its saturated solution determined through measuring absorbance. FIG. 8 shows the results. The water solubility of type I crystals was found to be 6.2 μg/mL, that of type II crystals 4.2 μg/mL, and that of the hydrate 1.9 μg/mL.

As is clear from FIG. 8, type I crystals and type II crystals have excellent water solubility. In particular, the water solubility of type I crystals is remarkably excellent.

The invention claimed is:

1. Type I crystals of 4-[5-(pyridin-4-yl)-1H-1,2,4-triazol-3-yl]pyridine-2-carbonitrile exhibiting characteristic peaks in powder X-ray diffractometry at diffraction angles 2θ of about 10.1°, 16.0°, 20.4°, 25.7°, and 26.7°.

2. A method for producing the type I crystals of claim 1, comprising:
   treating an acid salt of 4-[5-(pyridin-4-yl)-1H-1,2,4-triazol-3-yl]pyridine-2-carbonitrile with a base; and
   subsequently neutralizing the treated product with an acid.

* * * * *